(12) United States Patent
McLernon, III

(10) Patent No.: US 6,319,467 B1
(45) Date of Patent: Nov. 20, 2001

(54) ALLERGY TEST STRIP

(76) Inventor: William J. McLernon, III, 22-57 78th St., Astoria Heights, NY (US) 11370

( * ) Notice: Subject to any disclaimer, the term of this patent is extended or adjusted under 35 U.S.C. 154(b) by 0 days.

(21) Appl. No.: 08/229,910

(22) Filed: Apr. 19, 1994

(51) Int. Cl.⁷ .................................................. A61B 5/00
(52) U.S. Cl. ................................................. 422/58; 422/99
(58) Field of Search .................. 422/99, 58; 602/41–47, 602/54–59; 128/743; 604/116, 304, 307

(56) References Cited

U.S. PATENT DOCUMENTS

| | | | |
|---|---|---|---|
| 3,073,304 | * | 1/1963 | Schaar . |
| 3,894,531 | * | 7/1975 | Saunders, Jr. ........................ 128/743 |
| 3,999,504 | * | 12/1976 | Kearse ................................. 604/116 |
| 4,161,176 | * | 7/1979 | Harris, II et al. ..................... 128/155 |
| 4,228,796 | * | 10/1980 | Gardiner ............................... 604/116 |
| 5,099,857 | * | 3/1992 | Baldo et al. .......................... 128/743 |
| 5,158,555 | * | 10/1992 | Porzilli ................................. 128/155 |
| 5,254,109 | * | 10/1993 | Smith et al. ...................... 128/743 X |
| 5,308,313 | * | 5/1994 | Karami et al. ......................... 602/55 |
| 5,735,288 | * | 4/1998 | Fishman ............................... 128/743 |

\* cited by examiner

Primary Examiner—Jeffrey Snay
(74) Attorney, Agent, or Firm—Collard & Roe, P.C.

(57) ABSTRACT

A single allergy test strip is used in determining if a person has allergic reactions to allergens. A perforated layer of non-allergenic material has an adhesive layer on a back side thereof. The perforated layer has a top side with at least one perforation extending from the top side through the material and through the back side adhesive layer. A multilayer pad of allergy test strips contains several test strips each having an adhesive perimeter around the back edges thereof.

2 Claims, 2 Drawing Sheets

ALLERGY TEST STRIP

BACKGROUND OF THE INVENTION

1. Field of the Invention

The present invention relates to an allergy test strip for use in determining if a person has allergic reactions to allergens.

2. The Prior Art

It is known to test individuals for allergic reactions to various substances that produce these reactions and which are known as allergens. In the past, the testing protocols included applying to a selected area of the person's skin, one or more allergens and to determine what reaction, if any, did occur. Examples of these allergens include dust, mold spores, pollens (i.e., trees and grasses), foods, and insect bites.

Occasionally the medical person conducting the testing loses track of the location for some of the various allergens previously applied to the skin of the person being tested. This places into jeopardy the accuracy of the tests being conducted.

SUMMARY OF THE INVENTION

It is an object of the present invention to provide an allergy test strip that enables the tester to keep track automatically and very accurately of the allergens being administered to the skin of the person being tested.

The above object is achieved according to the present invention by providing an allergy test strip for use in determining if a person has allergic reactions to allergens, comprising a perforated layer of non-allergenic material having an adhesive layer on a back side thereof. The perforated layer has a top side with at least one perforation extending from the top side through the material and through the back side adhesive layer.

This invention will be used by the medical industry during the implementation of allergy testing. To be more specific, it is used during the eighty-four needle test (it may be adapted to other allergy tests as well). The allergy testing strip is made of two strips of non-allergenic material. One strip will be used on each forearm of the patient. Its shape is oblong, with dimensions of 2½ inches by 7 inches.

In a first embodiment, the allergy test strip is a single perforated layer of non-allergenic material having an adhesive layer covering the entire back side thereof with a removable, non-adhesive backing layer covering the bottom surface of the adhesive layer.

In a second embodiment, the allergy test strip is in the form of a multilayer pad having several test strips placed one on top of the other with an aligned adhesive perimeter running around the outside edges of each test strip on the back side thereof. Only the very bottom test strip has a non-adhesive backing layer thereon.

Down the left-hand side of the first strip appears the numbers 1 through 12, starting one inch from the top border and one-quarter of an inch from the left border (with one-half inch increments between each number). Across the top appear the letters A through D, one-half inch from the top border and one-half inch from the left-side border (with one-half inch increments between each letter). Parallel to the numbers and directly vertical to the letters, a one-quarter inch hole has been punched in the material, leaving a grid of 48 holes.

Down the side of the second strip appear the numbers 1 through 12, starting one inch from the top border and one-quarter of an inch from the left border (with one-half inch increments between each number). Across the top appear the letters A through C, one-half inch from the top border and one-half inch from the left-side border (with one-half inch increments between each letter). Parallel to the numbers and directly vertical to the letters, a one-quarter inch hole has been punched in the material, leaving a grid of 36 holes. When the allergy test strips are positioned on the forearm correctly, it will expose the area of skin that is to be used for the allergy test (i.e., allergens will be applied directly through exposed areas of the skin using the appropriate medical techniques).

The use of this device will reduce the preparation time for the medical staff. It will also give a more accurate test, due to the lack of confusion regarding allergenic inks now used in such testing methods.

BRIEF DESCRIPTION OF THE DRAWINGS

Other objects and features of the present invention will become apparent from the following detailed description considered in connection with the accompanying drawings which discloses the embodiments of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
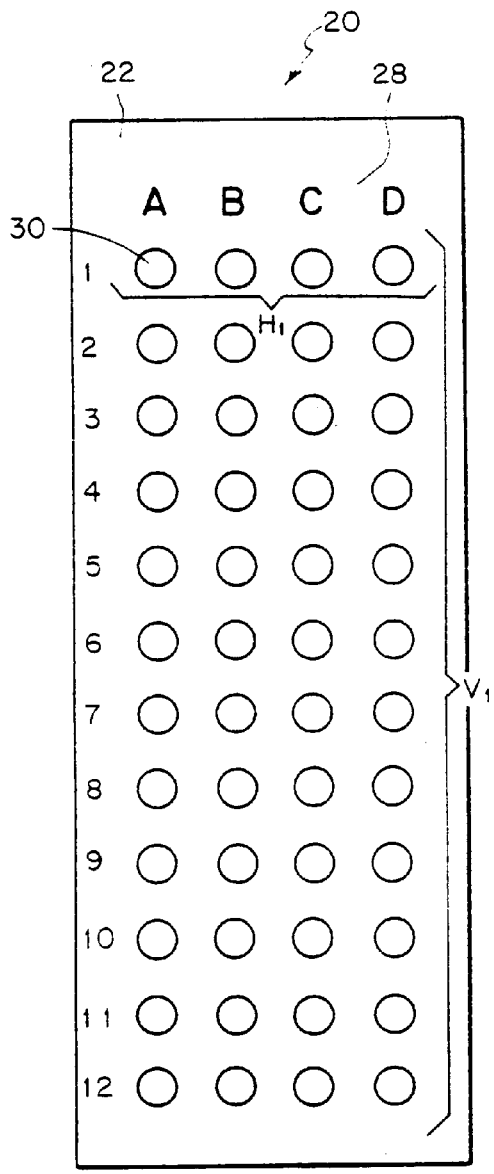
FIG. 1 shows a first embodiment of a single allergy test strip of the invention having 12 horizontal rows of openings and four vertical rows of openings.

Turning now in detail to the drawings, FIG. 1 shows a single allergy test strip 20 for use in determining if a person has allergic reactions to allergens. The strip 20 is a perforated layer 22 of non-allergenic material having an adhesive layer 24 on the back side 26 of the perforated layer.

Figure 4:
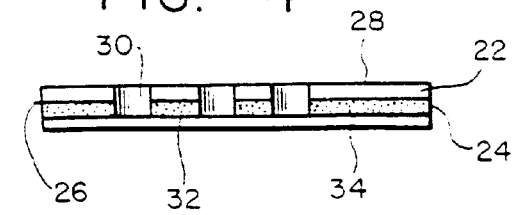
FIG. 4 shows a section view of the allergy test strip, taken along line 4—4 of FIG. 2.

FIG. 4 shows how the perforated layer 22 has a top side 28 with at least one opening, hole or perforation 30 extending from the top side 28 through the material of layer 22 and through adhesive layer 24 attached to the back side 26 of layer 22.

Figure 3:
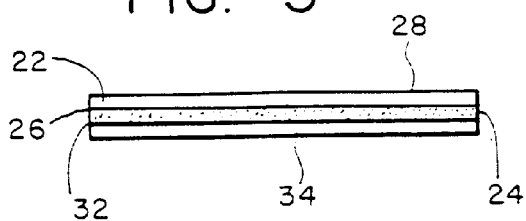
FIG. 3 shows an end view of the allergy test strip of FIG. 1.

As shown in FIGS. 3 and 4, the adhesive layer 24 has a bottom surface 32 with a removable non-adhesive backing layer 34 covering the bottom surface of the adhesive layer, for when the allergy test strip is not in use.

Figure 2:
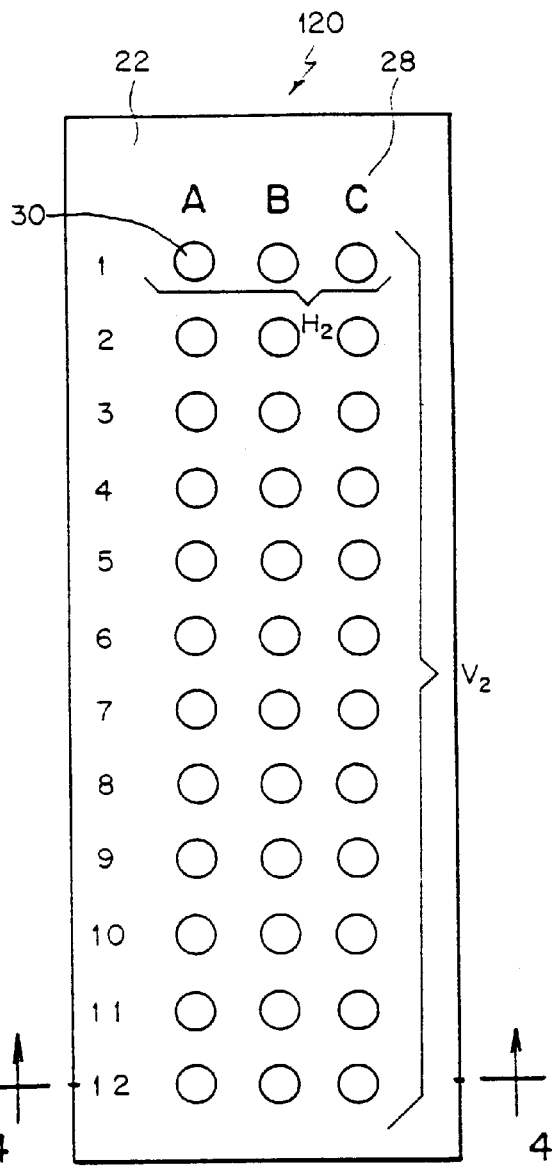
FIG. 2 shows a second embodiment of a single allergy test strip of the invention having 12 horizontal rows of openings and three vertical rows of openings.

FIGS. 1 and 2 show how the test strips 20 and 120 have several perforations 30 aligned in at least one horizontal row H1 in FIG. 1 and H2 in FIG. 2. In both FIGS. 1 and 2, there is a total of 12 horizontal rows. There is a first set of alphanumerical designations "A" through "D" for identifying each perforation 30 in the horizontal row H1 of test strip 20 of FIG. 1. There is also a first set of alphanumerical designations "A" through "C" for identifying each perforation 30 in the horizontal row H2 of test strip 120 of FIG. 2.

FIGS. 1 and 2 show how the test strips 20 and 120 have several perforations 30 aligned in at least one vertical row V1 in FIG. 1 and V2 in FIG. 2. In FIG. 1 there is a total of four vertical rows, while in FIG. 2 there is a total of three vertical rows. There is a second set of alphanumerical designations "1" through "12" for identifying each perforation 30 in the vertical row V1 of test strip 20 of FIG. 1 or in the vertical row V2 of test strip 120 of FIG. 2.

FIGS. 1 and 2 show that the first set of alphanumerical designations is different from the second strip of alphanumerical designations.

Figure 5:
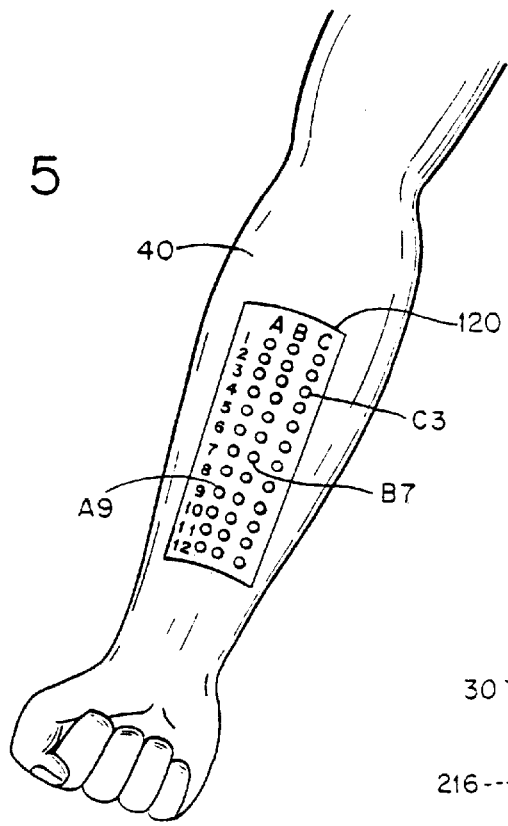
FIG. 5 shows the allergy test strip of FIG. 2 applied to the right forearm of the person to be tested.

FIG. 5 shows how the allergy test strip 120 of FIG. 2 would be applied to the right forearm 40 of a person for testing purposes. First, the non-adhesive backing 34 would be removed from the adhesive layer 24 which is then brought into contact with forearm 40. An accurate listing of the allergens applied to the skin of the forearm through perforations 30 can be compiled by defining each opening 30 with a pair of alphanumerical designations relating to the vertical row and the horizontal row, as illustrated in FIG. 5. Suitable examples of designation pairs include "A9," "B7" and "C3" with each pair correlated to a specific allergen applied to the forearm.

Figure 6:
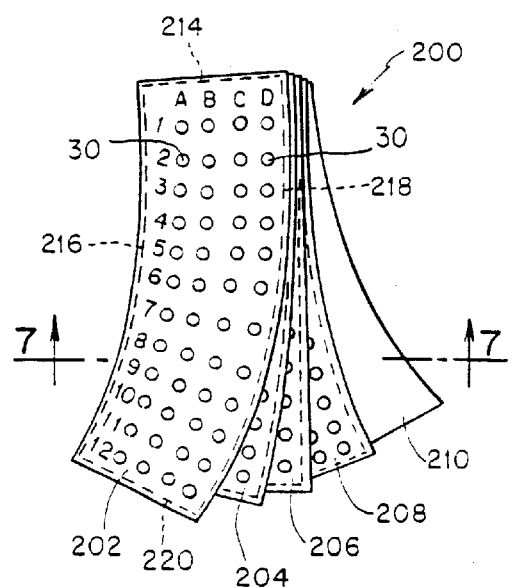
FIG. 6 shows a further embodiment in which a multi-player pad contains several allergy test strips.
Figure 7:
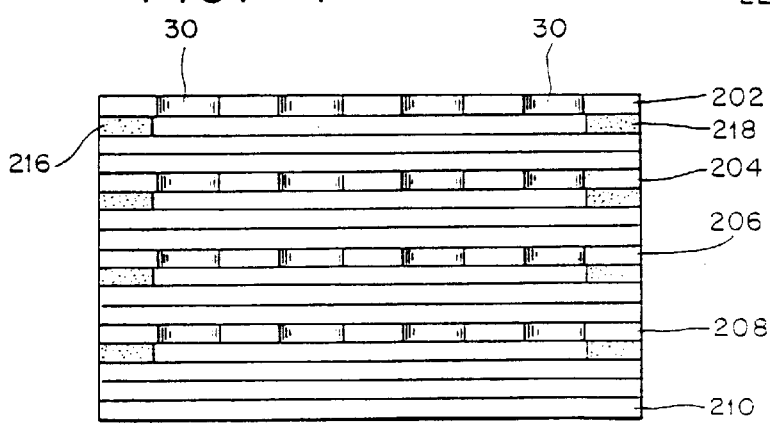
FIG. 7 shows a section view along line 7—7 of FIG. 6.

FIGS. 6 an d 7 show another embodiment in which a multilayer pad 200 is made up of several allergy test strips 202, 204, 206 and 208 placed one on top of the other. Test strip 202 is the top strip, test strip 208 is the bottom strip, and test strips 204 and 206 are intermediate test strips. Only the bottom strip 208 has a non-adhesive backing layer 210 thereon. There is an adhesive perimeter 212 running around the outside edges of each test strip on t he back side thereof.

Starting at the top 214 of the strip running horizontal from the right edge 218 to the left edge 216, a strip of adhesive one-half inch long from left to right will adhere the strips together as they will be produced in pads. At the bottom edge 220 the same one-half inch strip of adhesive will run along th e bottom edge, and from right side to left side. Along the left side outer edge 216 and along the right outer edge 218, a one-quarter inch strip of adhesive will be placed from top to bottom. The strips will come in pad format so each strip will be the backing for the previous strip. The bottom strip on the pad has the peelable backing 210. The entire back side of the strip will not be backed with adhesive, since only an adhesive perimeter is used in this embodiment.

While several embodiments of the present invention have been shown and described, it is to be understood that many changes and modifications may be made thereunto without departing from the spirit and scope of the invention as defined in the appended claims.

What is claimed is:

1. An allergy test strip for use in determining if a person has allergic reactions to allergens, consisting of a perforated layer of non-allergenic material having an adhesive layer on a back side thereof;

said perforated layer having a top side with several perforations extending from said top side through the material and through the back side adhesive layer;

wherein some of the several perforations are aligned in at least one horizontal row;

a first set of alphanumerical designations for identifying each perforation in the at least one horizontal row;

wherein some of the several perforations are aligned in at least one vertical row; and a second set of alphanumerical designations for each perforation in the at least one vertical row.

2. A multilayer pad of an allergy test strip for use in determining if a person has allergic reactions to allergens, consisting of several perforated layers of non-allergenic material, with each layer having an adhesive perimeter running around the outside edges of each test strip on a back side thereof;

each perforated layer having a top side with several perforations extending from said top side through the material and through the back side;

wherein some of the several perforations are aligned in at least one horizontal row;

a first set of alphanumerical designations for identifying each perforation in the at least one horizontal row;

wherein some of the several perforations are aligned in at least one vertical row;

a second set of alphanumerical designations for each perforation in the at least one vertical row; and each allergy test strip being placed one on top of the other with the adhesive perimeter aligned between each test strip perforated layer.

* * * * *